United States Patent [19]

Haven

[11] Patent Number: 4,695,024
[45] Date of Patent: Sep. 22, 1987

[54] TEST SYSTEM MANIPULATOR ARM

[75] Inventor: Kenneth R. Haven, Fremont, Calif.

[73] Assignee: Attain, Inc., Milpitas, Calif.

[21] Appl. No.: 861,189

[22] Filed: May 9, 1986

[51] Int. Cl.⁴ .............................................. E04G 3/00
[52] U.S. Cl. ............................ 248/281.1; 248/297.1; 403/85
[58] Field of Search .................. 248/281.1, 280.1, 278, 248/297.1, 123.1, 585; 403/85

[56] References Cited

U.S. PATENT DOCUMENTS

| | | | |
|---|---|---|---|
| 4,003,536 | 1/1977 | Sekerich | 248/585 |
| 4,082,244 | 4/1978 | Groff | 248/280.1 |
| 4,160,536 | 7/1979 | Krogsrud | 248/380.1 |
| 4,166,602 | 9/1979 | Nilsen et al. | 248/280.1 |
| 4,234,150 | 11/1980 | Mee et al. | 248/281.1 |
| 4,447,031 | 5/1984 | Souder et al. | 248/281.1 X |
| 4,548,373 | 10/1985 | Komura | 248/280.1 X |
| 4,568,052 | 2/1986 | Solomon et al. | 248/281.1 |

Primary Examiner—Ramon O. Ramirez
Attorney, Agent, or Firm—Walter J. Madden, Jr.; Alan H. MacPherson; Paul J. Winters

[57] ABSTRACT

An adjustable arm for controlling the horizontal and vertical position of an object mounted at one end of the arm comprises:

means for rigidly mounting the end of the arm opposite the end at which the object is mounted;

a plurality of interconnected links, a first group of the plurality of links controlling the horizontal position of the arm and the object; and a counterbalancing link among the plurality of links, the counterbalancing link being disposed intermediate the first group of links, the counterbalancing link serving to provide vertical movement of the plurality of links and the object and to counterbalance the weight of the object at the one end of the arm.

4 Claims, 3 Drawing Figures

TEST SYSTEM MANIPULATOR ARM

BACKGROUND OF THE INVENTION

1. Field of the Invention

This invention relates to a device for use in testing integrated circuits and is in the form of a movable arm having a series of links with integral adjustable mechanisms for "weightless" positioning of a test head.

2. Prior Art

Other test head manipulators exist in the form of movable arms, usually with some type of weight to counterbalance the weight of the test head, but have one or more of the following disadvantages:
   (1) Limited range of motion in the horizontal plane;
   (2) No provision for cable handling;
   (3) Large floorspace "footprint"; and
   (4) Potential safety hazard when the test head is removed with the counterbalance mechanism active.

Other manipulators for use in dental and general purpose applications exist, but they have the following problems:
   (1) No provision for cable handling;
   (2) Potential safety hazard when the head is removed with the counterbalance mechanism active; and
   (3) Insufficient load capability.

SUMMARY OF THE PRESENT INVENTION

This invention solves the above problem as follows:
   (1) Links are of sufficient length and their arrangement is configured to allow the head to be brought to device handlers, etc., without the preliminary step of relocating a manipulator frame into a rough position.
   (2) Cable troughs are provided to protect and locate the cable bundle between the test station and the head. Motion of the arm is designed to provide gentle bending of the cable bundle.
   (3) The arm uses the structure and mass of the test station for its mounting, and hence requires no floorspace for a support frame.
   (4) Counterbalancing is by means of a gas spring, which is inherently self-damping. The spring energy cannot be released suddenly and hazardously as with metal springs or weight counterbalances.
   (5) The strength and stiffness of the arm is designed to safely support and counterbalance a total load of 100 pounds.

DESCRIPTION OF THE PREFERRED EMBODIMENT

Figure 1:
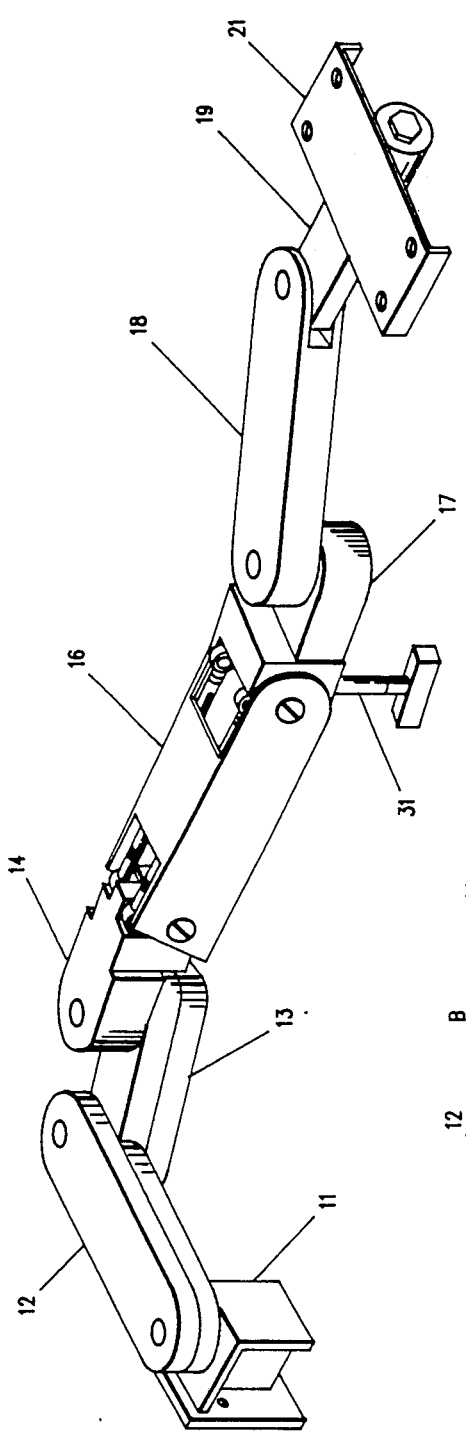
FIG. 1 is a perspective view showing the components of a manipulator arm in accordance with the present invention.
Figure 2:
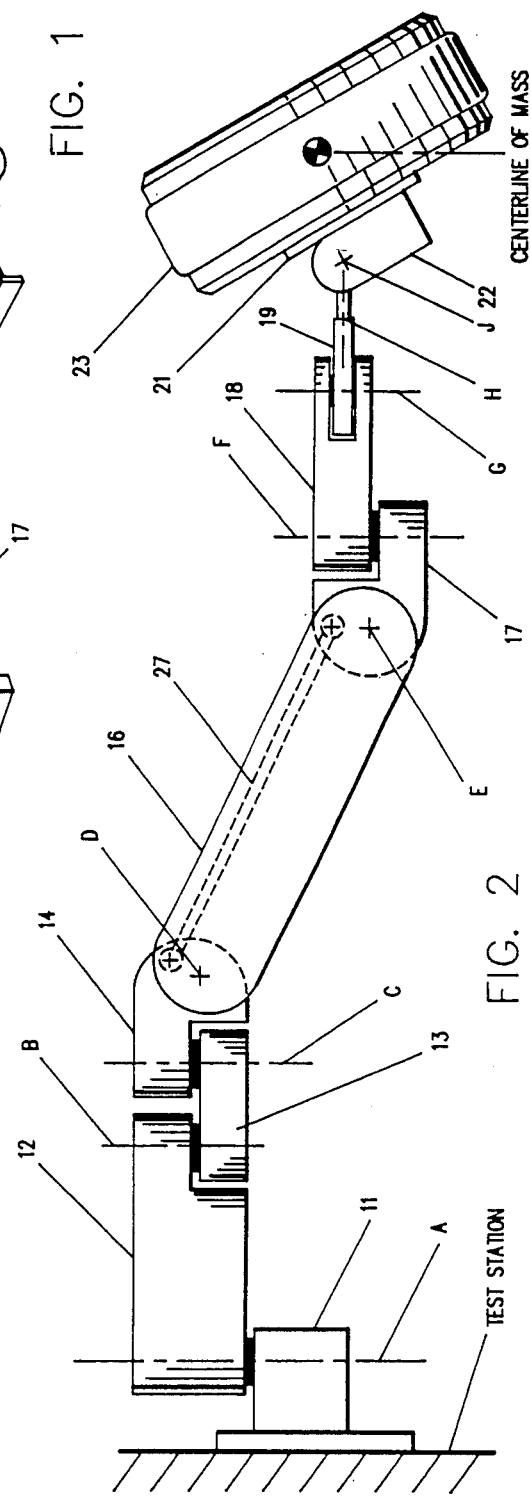
FIG. 2 is a side view of the arm of FIG. 1 illustrating the different axes of movement of the arm components.

Referring to the perspective view of the arm of the present invention shown in FIG. 1, reference numeral 11 designates a base link which is firmly attached to the test station. Pivotally connected to base line 11 is a link 12. Link 12 is pivotally connected to a link 14 through a link 13. Link 14 in turn is connected to a chain of links including link 16, link 17, link 18, and link 19. Link 19 is connected through a knuckle joint (more clearly seen in FIG. 2) to a plate 21 for holding the test head to be manipulated. Referring to FIG. 2, and as mentioned above, base link 11 is rigidly attached to the test station, which has sufficient mass and strength to provide full support of up to two arms with attached test heads and cabling, at any orientation of the arms and heads. Up to four arms can be supported by extending the mounting feet of the test station or by attaching the test station to the floor.

Link 12 pivots about vertical axis A. Axes B and C are coupled together through gearing to form a single imaginary vertical axis connecting links 14 and 12, allowing a full 360 degress rotation while maintaining a gentle cable bend radius. Links 14, 16 and 17 move as a single unit with respect to vertical axis BC. Link 18 moves about vertical axis F, and link 19, the knuckle joint 22 and test head 23 move about vertical axis G. These four vertical axes provide complete freedom of motion in the horizontal plane, and allow an extra degree of freedom to allow choice in the path of the arm for clearing obstacles.

Vertical motion is provided by links 14 and 17 being interconnected through link 16 and internal tie bars internal to link 16 (FIG. 3) to form a parallelogram assembly with horizontal axes D and E. Thus links 17, 18 and 19 remain horizontal and their interconnecting axes F and G remain vertical so that further counterbalancing is not required. The knuckle joint 22 provides adjustable friction to prevent unwanted motion about nonvertical axes H and J. The knuckle joint allows inversion of the test head 23, and also the setting of any head angle required by an application. In an alternate embodiment, a yoke assembly could replace the knuckle joint.

Figure 3:
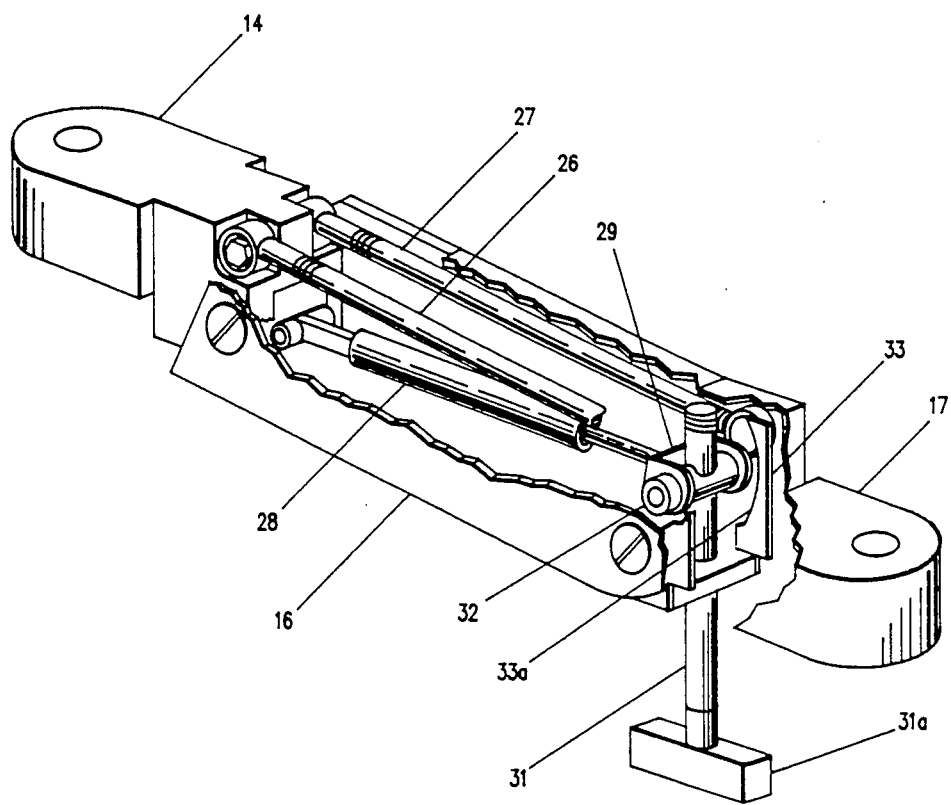
FIG. 3 is a perspective view, partly broken away, showing the structure of the portion of the arm containing the gas spring.

FIG. 3 is a perspective view, partly broken away, showing link 16, a key element of the invention. Link 16 includes a pair of tie bars 26, 27 extending essentially the length of link 16 which operate in a well known manner to form a parallelogram motion mechanism. Link 16 also includes a gas spring 28 whose spring force can be adjusted to exactly counterbalance the weight of the test head 23. Gas spring 28 may be of any suitable type, such as those manufactured by Supss-Federungstechnik of Altdorf, West Germany. The distal end of spring 28 is anchored to link 14 while the piston rod end of the spring is connected to a mechanism for adjusting the counterbalancing force supplied by the spring. This mechanism includes a yoke 29 to which the piston rod portion of spring 28 is attached. The vertical position of yoke 29 can be adjusted by means of a threaded adjusting rod 31 which extends through a tapped opening in yoke 29. Rotation of rod 31 by means of its handle 31a changes the vertical position of yoke 29. Associated which yoke 29 are a pair of rollers 32 which ride on a ramped or camming surface 33a of a plate 33. Rotation of rod 31 will vary the portion of ramped surface 33a on which rollers 32 ride and will thus vary the position of yoke 29 on the horizontal axis of spring 28. This in turn will vary the position of piston rod portion 28a of spring 28 and thus vary the force exerted by spring 28.

In operation, rod 31 is turned to cause the force exerted by spring 28 to exactly counterbalance the weight of the particular test head 23 in place on the arm. Once so adjusted, no further adjustment is required as long as that particular test head remains on the arm. If a different test head having a different weight is to be placed on the arm, the force exerted by spring 28 may be adjusted by rotation of rod 31 to provide exact counterbalancing for the weight of the new test head.

Since the gas spring is very nearly a constant force device, the counterbalance force cannot be varied over a wide range by changing the spring compression, as is done with conventional steel spring counterbalance mechanisms. This invention instead changes the spring pivot point (and therefore its lever arm) over a path to allow convenient external force adjustments over a range of 0 to 100 pounds, whenever needed. This path was computer-optimized for minimum counterbalance force error over the adjustment range.

This invention would apply (scaled approximately) to any counterbalanced positioning applications, such as dental office x-ray equipment, medical electronics and displays in surgery, CRT and computer workstations, to name a few.

I claim:

1. An adjustable arm for controlling the horizontal and vertical position of an object mounted at one end of said arm, said arm comprising:
   means for rigidly mounting the end of said arm opposite said end at which said object is mounted;
   a plurality of interconnected links, a first group of said plurality of links controlling the horizontal position of said arm and said object;
   a counterbalancing link among said plurality of links, said counterbalancing link being disposed intermediate said first group of links, said counterbalancing link serving to provide vertical movement of said plurality of links and said object and to counterbalance the weight of said object at said one end of said arm;
   said counterbalancing link including a gas spring for supplying a counterbalancing force;
   means for adjusting the counterbalancing force supplied by said gas spring; and
   said adjusting means including a ramped surface for controlling the force supplied by said gas spring.

2. Apparatus in accordance with claim 1 including roller means connected to one end of said gas spring, said roller means riding on said ramped surface; and
   means for adjusting the portion of said ramped surface on which said roller means ride to thereby adjust the counterbalancing force supplied by said gas spring.

3. Apparatus in accordance with claim 2 in which said gas spring has a distal end and a piston rod end, said roller means being connected to said piston rod end of said spring to vary the position of said piston rod in said spring as a function of the position of said roller means on said ramped surface.

4. Apparatus in accordance with claim 3 in which said distal end of said gas spring is connected to one of said first group of links.

* * * * *